US010765798B2

(12) United States Patent
Mackelfresh et al.

(10) Patent No.: US 10,765,798 B2
(45) Date of Patent: Sep. 8, 2020

(54) FEEDING SYRINGE HOLDER (71) Applicant: Medline Industries, Inc., Northfield, IL (US)

(72) Inventors: Timothy Mackelfresh, Lake Zurich, IL (US); Morgan Uridil, Evanston, IL (US)

(73) Assignee: Medline Industries, Inc., Northfield, IL (US)

( * ) Notice: Subject to any disclaimer, the term of this patent is extended or adjusted under 35 U.S.C. 154(b) by 0 days.

(21) Appl. No.: 16/256,414

(22) Filed: Jan. 24, 2019

(65) Prior Publication Data
US 2020/0238001 A1    Jul. 30, 2020

(51) Int. Cl.
*A61M 5/14* (2006.01)
*A61J 9/06* (2006.01)
*A61J 15/00* (2006.01)

(52) U.S. Cl.
CPC .............. *A61M 5/1417* (2013.01); *A61J 9/06* (2013.01); *A61J 15/0026* (2013.01)

(58) Field of Classification Search
CPC .. A61M 5/1417; A61M 5/008; A61J 15/0026; A61J 9/06; A47B 2051/005; B65D 23/003; B65D 25/22; A47G 23/0241; A47G 7/044; B67D 3/0029; A61B 50/20
See application file for complete search history.

(56) References Cited

U.S. PATENT DOCUMENTS

| 1,607,053 | A | * | 11/1926 | Buchanan | ........... | A61M 5/1417 |
| | | | | | | 294/31.2 |
| 2,756,740 | A | * | 7/1956 | Deane | ................. | A61J 15/0011 |
| | | | | | | 604/77 |
| 2,760,262 | A | * | 8/1956 | Homan | ............... | A61M 5/1417 |
| | | | | | | 29/513 |
| 2,982,434 | A | * | 5/1961 | Hidding | .............. | A61M 5/1417 |
| | | | | | | 215/398 |
| 3,195,759 | A | * | 7/1965 | Beacham | ............ | A61M 5/1417 |
| | | | | | | 215/399 |

(Continued)

FOREIGN PATENT DOCUMENTS

| EP | 2434635 | 3/2012 |
| EP | 3325044 | 5/2018 |

(Continued)

OTHER PUBLICATIONS

Medline Industries, Inc., Pictures of Medline EntraFlo Nutrition Delivery System, publicly available Nov. 1, 2018.

(Continued)

*Primary Examiner* — Christopher Garft
(74) *Attorney, Agent, or Firm* — Fitch, Even, Tabin & Flannery LLP (57) ABSTRACT

In one aspect, a system is provided for administering a formulated food solution. The system includes a syringe body having a collar, a barrel, and at least one protrusion. The system includes a handle configured to be hung on a support and a holder body connected to the handle. The holder body has a central opening sized to receive the syringe body. The holder body includes at least one alignment portion configured to engage at least one protrusion of the syringe body and resist turning of the syringe body in the central opening of the holder body.

19 Claims, 7 Drawing Sheets

(56) References Cited

U.S. PATENT DOCUMENTS

| | | | | |
|---|---|---|---|---|
| 3,220,591 | A | * | 11/1965 | Hidding .............. A61M 5/1417 215/399 |
| 3,556,453 | A | * | 1/1971 | Hall ...................... B63B 29/12 248/311.2 |
| 3,630,477 | A | * | 12/1971 | Stadler ............... A61M 5/1417 248/318 |
| 3,638,823 | A | * | 2/1972 | McCoy ............... A61M 5/1417 215/399 |
| 3,807,679 | A | * | 4/1974 | Burke ............... A47G 23/0241 248/690 |
| 4,045,070 | A | * | 8/1977 | Geisinger ................ A61J 1/16 294/31.2 |
| 4,634,089 | A | * | 1/1987 | Wright .................. B60N 3/103 248/205.2 |
| 5,135,125 | A | * | 8/1992 | Andel ................ A61M 5/1417 215/12.1 |
| 5,174,534 | A | * | 12/1992 | Mitchell ............... B60N 3/103 215/395 |
| 5,470,037 | A | | 11/1995 | Willis |
| 5,490,658 | A | * | 2/1996 | Coward ............. A61M 5/1417 215/399 |
| 5,514,102 | A | | 5/1996 | Winterer |
| 5,647,520 | A | * | 7/1997 | McDaid .................. B62J 11/00 224/425 |
| 5,720,721 | A | | 2/1998 | Dumas |
| 5,934,222 | A | * | 8/1999 | Hwang .................... A01K 7/06 119/51.03 |
| 6,129,703 | A | | 10/2000 | Beneke |
| 6,435,134 | B1 | * | 8/2002 | Ho ...................... A01K 1/0356 119/464 |
| 6,561,129 | B1 | * | 5/2003 | Cheng ................. A01K 1/0356 119/72 |
| 7,092,797 | B2 | | 8/2006 | Gaines |
| 7,447,566 | B2 | | 11/2008 | Knauper |
| 7,726,174 | B2 | | 6/2010 | Riley |
| 7,763,005 | B2 | | 7/2010 | Knauper |
| 7,818,992 | B2 | | 10/2010 | Riley |
| 8,021,322 | B1 | | 9/2011 | Francis |
| 8,142,404 | B2 | | 3/2012 | Knauper |
| 8,225,639 | B2 | | 7/2012 | Riley |
| 8,574,190 | B2 | | 11/2013 | Francis |
| 9,101,712 | B2 | | 8/2015 | Denis |
| 9,402,789 | B2 | | 8/2016 | Knauper |
| 9,408,968 | B2 | | 8/2016 | Browne |
| 9,424,020 | B2 | | 8/2016 | Borges |
| 9,710,610 | B2 | | 7/2017 | Flynn |
| 9,820,916 | B2 | | 11/2017 | Boulanger |
| 9,852,263 | B2 | | 12/2017 | Harr |
| 9,871,866 | B2 | | 1/2018 | Borges |
| 9,909,688 | B2 | | 3/2018 | Gaines |
| 9,974,902 | B2 | | 5/2018 | Holderle |
| 10,215,305 | B2 | | 2/2019 | Gaines |
| 10,219,985 | B2 | | 3/2019 | Hudson |
| 10,227,971 | B2 | | 3/2019 | Hudson |
| 10,293,103 | B2 | | 5/2019 | Adams |
| 10,387,624 | B2 | | 8/2019 | Jedwab |
| 10,426,709 | B2 | | 10/2019 | Harr |
| 2008/0119822 | A1 | | 5/2008 | Knauper |
| 2010/0057017 | A1 | | 3/2010 | Pappas |
| 2013/0161470 | A1 | * | 6/2013 | Alvares .................. B65D 25/32 248/318 |
| 2016/0058673 | A1 | | 3/2016 | Francis |
| 2016/0235630 | A1 | | 8/2016 | Zuijderduin |
| 2016/0361492 | A1 | | 12/2016 | Nunez |
| 2017/0197026 | A1 | | 7/2017 | Kesselman |
| 2018/0207360 | A1 | | 7/2018 | Juretich |
| 2018/0234499 | A1 | | 8/2018 | Borges |
| 2018/0236168 | A1 | | 8/2018 | Holderle |
| 2019/0142699 | A1 | | 5/2019 | Hudson |
| 2019/0216688 | A1 | | 7/2019 | Ganter |
| 2019/0240397 | A1 | | 8/2019 | Adams |
| 2019/0358387 | A1 | | 11/2019 | Elbadry |

FOREIGN PATENT DOCUMENTS

| | | |
|---|---|---|
| WO | 2008059495 | 5/2008 |
| WO | 2016152238 | 9/2016 |
| WO | 2018177765 | 10/2018 |
| WO | 2019148900 | 8/2019 |

OTHER PUBLICATIONS

SideKick Solo, Feeding Tube Stand, http://sidekicksolo.com/sidekick-solo/, Accessed on Nov. 6, 2018.

* cited by examiner

FIG. 7

FEEDING SYRINGE HOLDER

FIELD

The present disclosure relates to patient enteral feeding systems and, more particularly, to a patient enteral feeding system that utilizes gravity to draw feeding solution out of a syringe body of the system and into a feeding tube of a patient.

BACKGROUND

Percutaneous endoscopic gastronomy tubes are used to convey a formulated food solution into a patient's stomach if the patient is unable to swallow food. In one approach, a syringe body is used as a reservoir that receives the formulated food solution. The syringe body has a tip that is connected to a tube for conveying the formulated food solution to a feeding tube implanted in the patient. The feeding tube delivers the formulated food solution directly into the patient's stomach.

One prior approach includes a rigid stand with a projecting arm that receives the syringe body and holds the syringe body at a higher vertical position than the outlet of the tube connected thereto. The stand has a C-clamp that receives the syringe body that holds the syringe body upright. However, rigid stands are often difficult to use and take up space around a patient's home.

DETAILED DESCRIPTION

In one aspect of the present disclosure, a holder is provided for a syringe body of a formulated food solution delivery system. The holder includes a handle configured to be hung on a support and a body connected to the handle. The body has a central opening for receiving a barrel of a syringe body and is configured to keep the syringe body upright with the handle hung on the support. The body includes at least one alignment portion of the body configured to engage at least one protrusion of the syringe body and resist turning of the syringe body in the central opening of the body.

In another aspect of the present disclosure, a system is provided for administering a liquid food product. The system includes a syringe body having a collar, a barrel, and at least one protrusion. The system includes a handle configured to be hung on a support and a holder body connected to the handle. The holder body has a central opening sized to receive the syringe body. The holder body includes at least one alignment portion configured to engage at least one protrusion of the syringe body and resist turning of the syringe body in the central opening of the holder body.

Figure 1:
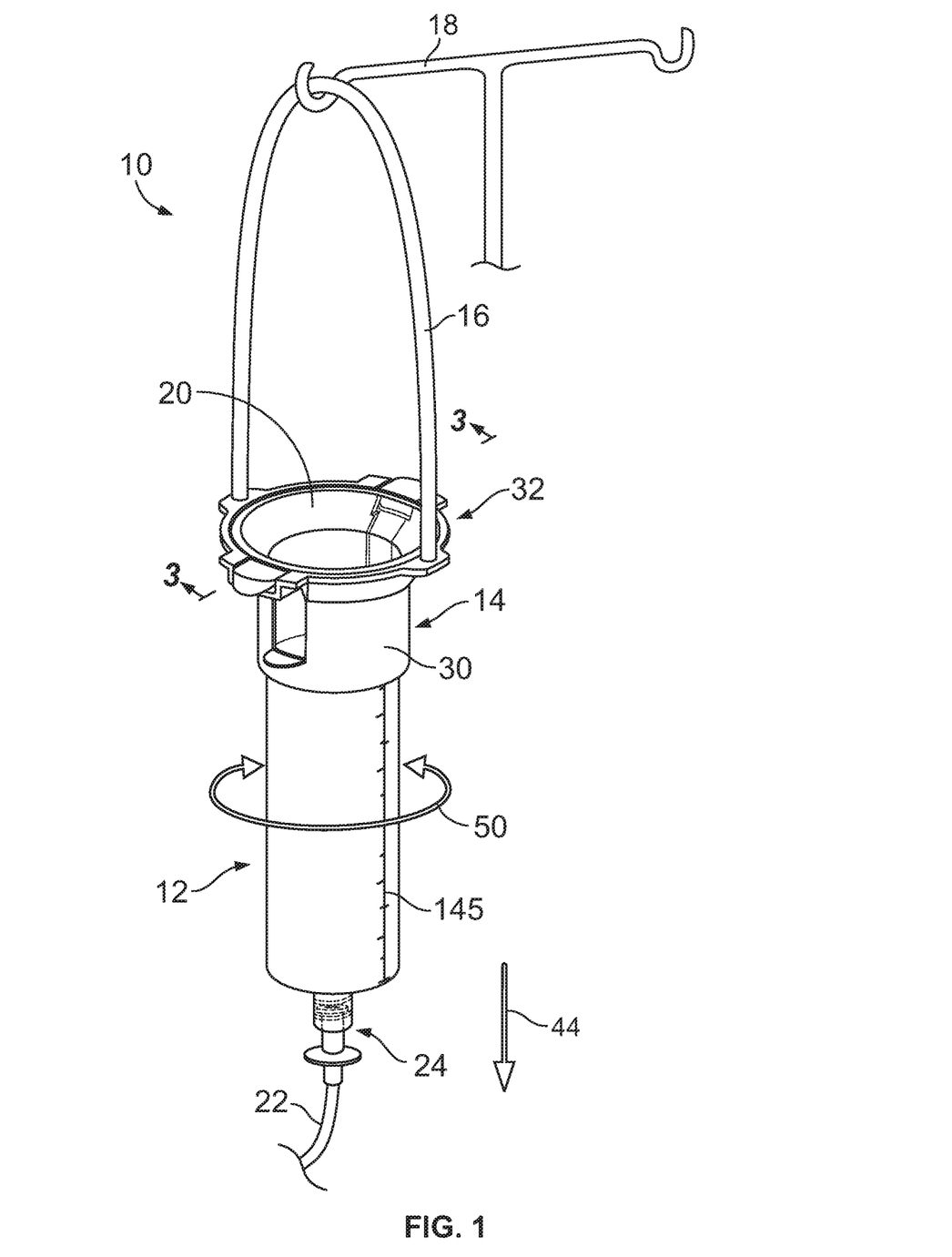
FIG. 1 is a perspective view of a formulated food solution delivery system including a holder having a handle hung on an intravenous pole and a syringe body received in the holder.

With reference to FIG. 1, a formulated food solution delivery system 10 is provided that includes a syringe body 12 for receiving a formulated food solution and a holder 14 having a handle 16 configured to be hung from a structure, such as an intravenous pole 18. The syringe body 12 may be configured to receive, for example, 60 cc of formulated food solution. The holder 14 includes a body 30 and a releasable connection 32 between the handle 16 and the body 30.

The syringe body 12 includes an upper opening 20 for receiving the formulated food solution and a tip 26 (see FIG. 2) configured to connected to a tube 22 via a connector 24. During use, the tube 22 is placed in communication with a patient's feeding tube and gravity draws the formulated food solution from within the syringe body 12, into the tube 22, into the patient's feeding tube, and into the patient's stomach. In one embodiment, the tip 26 includes a male thread. In another embodiment, the tip 26 may be connected to the tube 22 via a EnFit connection.

Figure 2:
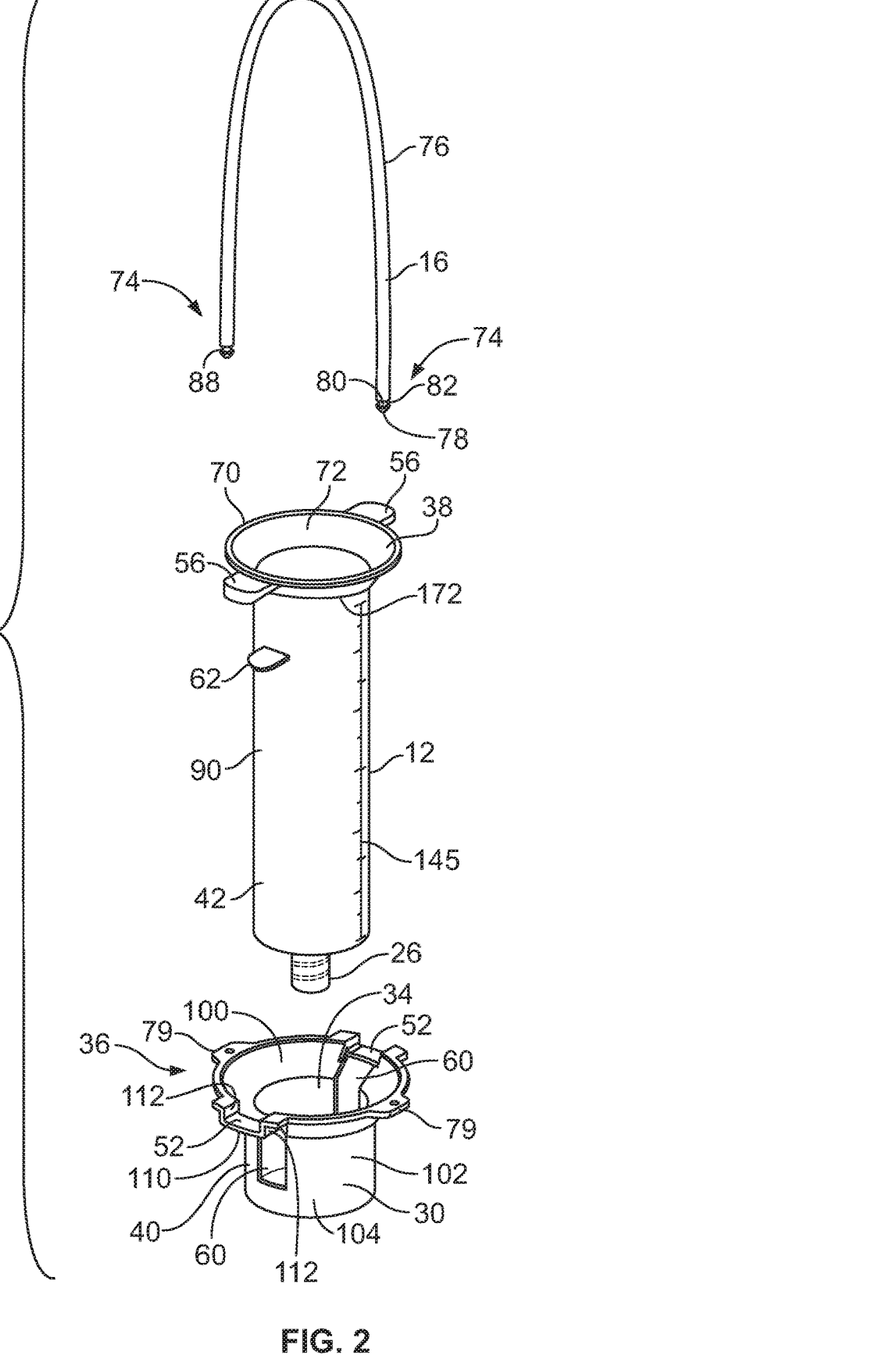
FIG. 2 is an exploded perspective view of the holder and syringe body of FIG. 1 showing the handle of the holder separated from a body of the holder.

Regarding FIGS. 1 and 2, the body 30 may have a generally tubular configuration with a central opening 34 that receives the syringe body 12. The body 30 includes an upper, collar-receiving portion 36 against which a collar 38 of the syringe body 12 seats. The body 30 further includes a lower, barrel-receiving portion 40 that extends around a barrel 42 of the syringe body 12. The upper, collar-receiving portion 36 resists movement of the syringe body 12 in direction 44 (see FIG. 1) and keeps the syringe body 12 securely held at the desired vertical position. One or more of the upper, collar-receiving portion 36 and the lower, barrel-receiving portion 40 includes at least one alignment portion that restricts rotary movement of the syringe body 12 in direction 50 within the body 30. In this manner, the body 30 provides a stable support for the syringe body 12 and resists any shifting of the syringe body 12, such as due to movement of the tube 22 due to patient movement.

In one embodiment, the at least one alignment portion includes one or more pockets 52 of the body 30 as shown in FIG. 2. The pockets 52 each receive a projection, such as an upper tab 56, of the syringe body 12. The at least one alignment portion may also include one or more openings 60 of the body 30. The openings 60 each receive a projection, such as a lower tab 62, of the syringe body 12. The collar 38 of the syringe body 12 includes a flange or rim 70, a frustoconical wall 72 extending radially inward from the rim 70, and the tabs 56 extending radially outwardly from the rim 70.

The handle 16 includes a pair of opposite end portions 74 and a loop portion 76 extending therebetween. Each end portion 74 includes a head portion 78, a neck portion 80, and a gap 82 extending around the neck portion 80. The upper, collar-receiving portion 36 of the body 30 of the holder 14 includes tabs 79 with openings 84 (see FIG. 4) that receive the head portions 78 of the handle 16. In one approach, the head portions 78 of the handle 16 each have a maximum diameter thereacross that is slightly larger than a diameter of the associated opening 84 of the tab 79.

To connect the handle end portion 74 to one of the tabs 79, the head portion 78 is advanced into the opening 84 of the tab 79 until the head portion 78 snaps below the tab 79. With the head portion 78 below the tab 79, the head portion 78 has an upper surface 88 that contacts a lower surface 81 (see FIG. 5) of the tab 79 and supports the body 30. The neck portion 80 extends through the opening 84 and has an outer diameter slightly smaller than the opening 84 to provide a snug fit of the neck portion 80 in the opening 84. The connection between the handle end portions 74 and the tabs 79 of the body 30 orients the handle end portions 74 so that the handle end portions 74 each extend generally normal to the associated tab 79. By generally normal, it is intended that there may be a slight curvature or angulation of the handle end portion 74 from normal as the handle end portion 74 extends away from the tab 79, such as an angulation of between 0.1 and 15 degrees from normal.

Regarding FIG. 2, the barrel 42 of the syringe body 12 includes an annular side wall 90 and the lower tabs 62 project radially outward from the side wall 90. In one embodiment, the upper tabs 56 and the lower tabs 62 are vertically aligned so that both the upper tabs 56 and lower tabs 62 advance into the openings 60 on the opposite sides of the body 30 as the syringe body 12 is positioned in the holder 14. In one embodiment, the upper, collar-receiving portion 36 of the holder 14 includes a frustoconical wall portion 100 that extends around and supports the collar 38 of the syringe body 12 once the syringe body 12 has been positioned in the opening 34 of the body 30. The body 30 also includes a sleeve 102 that extends around the barrel 42 of the syringe body 12. The inner diameter of the sleeve 102 is sized slightly larger than the outer diameter of the barrel 42 so that the barrel 42 is firmly received within the sleeve 102. In one approach, the sleeve 102 includes a collar portion 104 that extends completely around the barrel 42 without interruption to provide a stable connection between the body 30 of the holder 14 and the syringe body 12.

Figure 3:
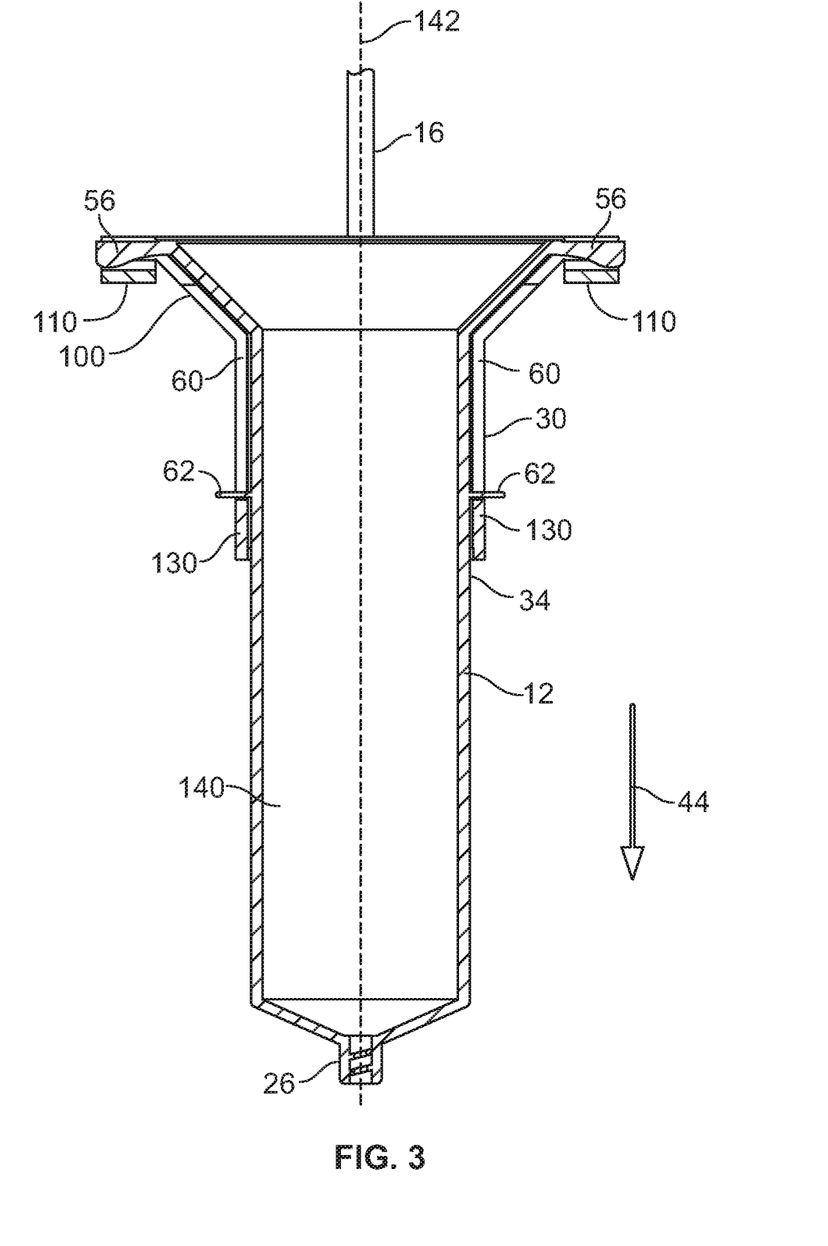
FIG. 3 is a cross-sectional view taken across line 3-3 in FIG. 1 showing lower tabs of the syringe body extending laterally outward through openings of the holder body and upper tabs of the syringe body received in pockets of the holder body.
Figure 5:
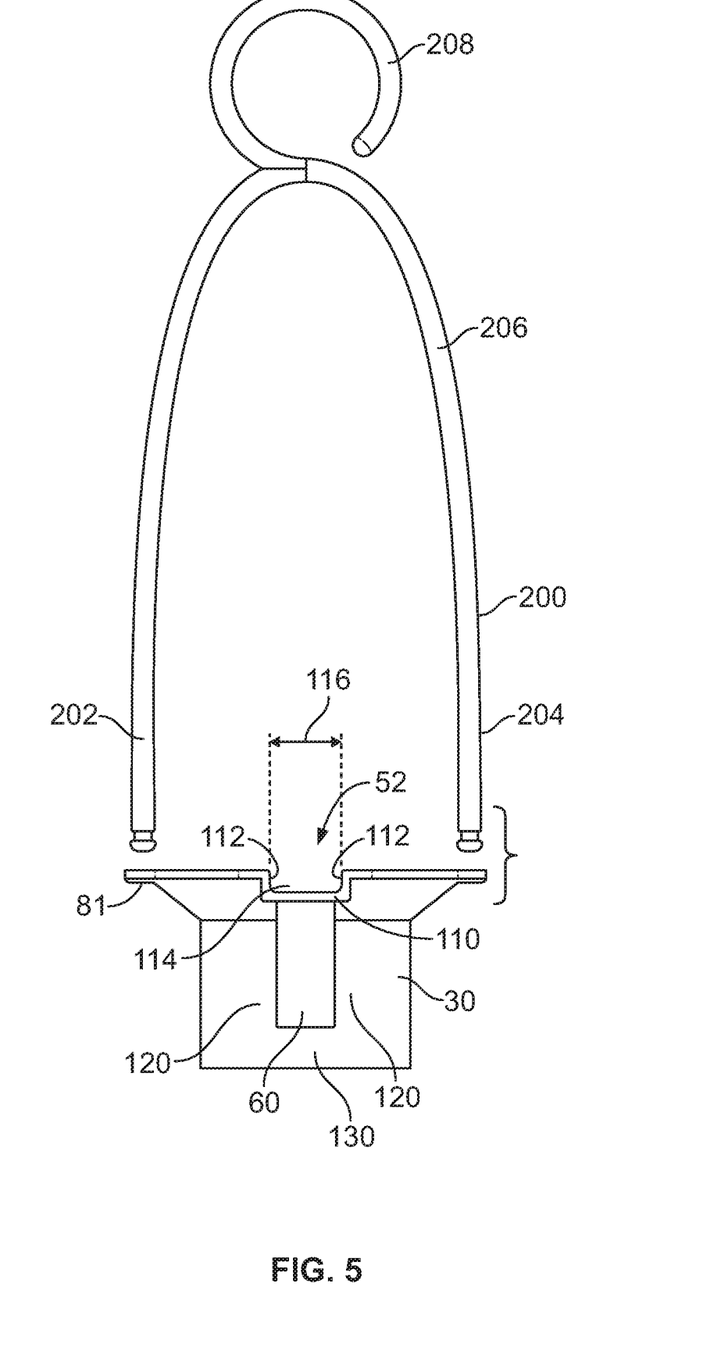
FIG. 5 is an elevational, exploded view of another holder with a handle that includes a hook.

With reference to FIGS. 2 and 3, each pocket 52 of the body 30 includes a floor 110 that extends below the associated upper tab 56 of the syringe body 12 and a pair of side walls 112 that extend upward along opposite sides of the upper tab 56. With reference to FIG. 5, the side walls 112 are separated by a gap 114 having a distance 116 sized to permit the upper tab 56 to be advanced downwardly into the gap 114 and seated against the floor 110. The sleeve 102 includes wall portions 120 on opposite sides of the opening 60. When one of the lower tabs 62 of the syringe body 12 is received in the opening 60, the lower tab 62 will contact or be adjacent to the wall portions 120. In this manner, contact between the lower tab 62 and one of the wall portions 120 resists turning of the syringe body 12 in direction 50 relative to the body 30.

Turning to FIGS. 3 and 5, the lower tabs 62 of the syringe body 12 may seat against bridge portions 130 of the body 30 that connect the wall portions 120. Further, the upper tabs 56 of the syringe body 12 seat against the floors 110 of the pockets 52 of the body 30. This engagement resists movement of the syringe body 12 in direction 44 (see FIG. 1) under the weight of the formulated food solution in an internal volume 140 of the syringe body 12. Regarding FIG. 3, the central opening 34 of the body 30 extends along a longitudinal axis 142 and the upper and lower tabs 56, 62 of the syringe body 12 extend laterally outward onto the floors 110 and the bridge portions 130 of the body 30.

In one embodiment, the body 30 has an axial length that is less than half of the axial length of the syringe body 12. This permits the tip 26 to be exposed for ready connection to the tube 22 as shown in FIGS. 1 and 2. This also permits viewing of a measurement indicium, such as calibrations 145, on the exterior of the barrel 42 of the syringe body 12. In this manner, a patient may readily visually confirm that the syringe body 12 has been filled with the desired volume of formulated food solution.

Figure 4:
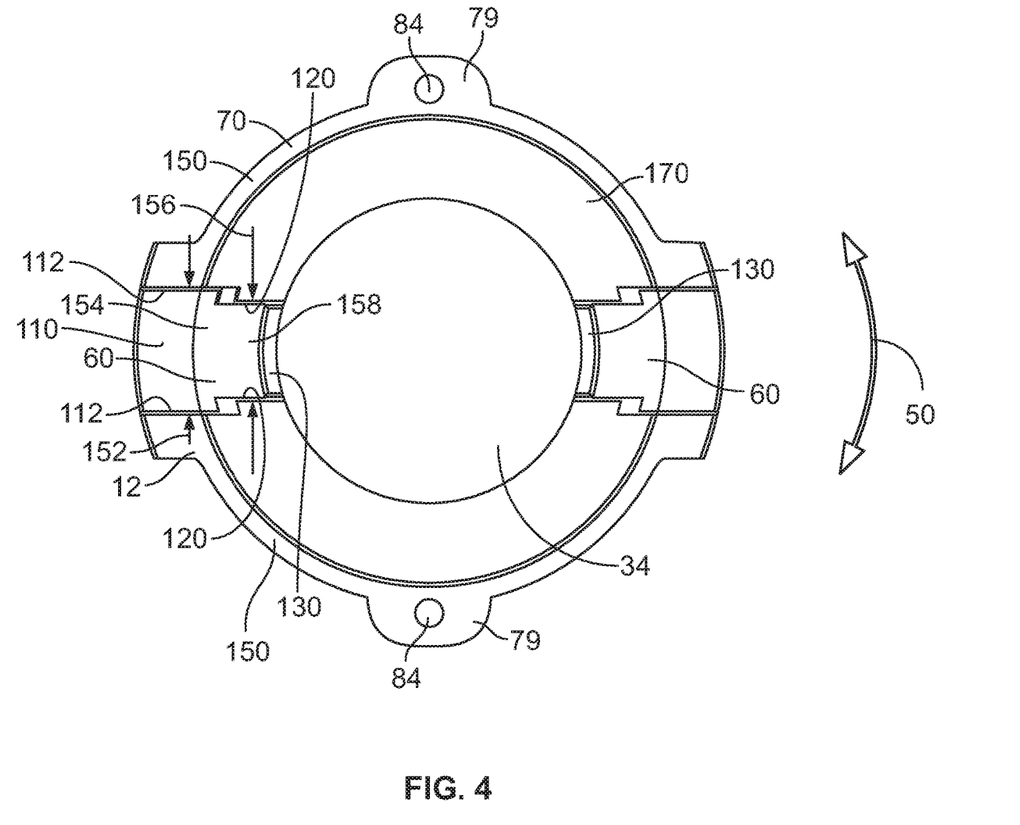
FIG. 4 is a top plan view of the holder body of FIG. 2 showing diametrically opposed openings of the holder body that receive the upper and lower tabs of the syringe body.

Regarding FIG. 4, the rim 70 of the syringe body 12 includes halves 150 separated by the openings 60. Each opening 60 includes a wide first portion 154 having a width 152 and a narrow second portion 158 having a width 156 that is less than the width 152. The different widths 152, 156 form a notched configuration of each of the openings 60. Further, the wide first portion 154 may accommodate a wider upper tab 56 while the narrow second portion 158 may more closely conform to the width of one of the narrower lower tabs 62. The body 30 of the holder 14 may thereby complement the protruding features of the syringe body 12.

As shown as in FIG. 4, the frustoconical wall 72 of the body 30 includes at least one upwardly facing upper surface 170. The upper surface 170 has a taper that matches the taper of a lower surface 172 of the collar 38 of the syringe body 12 (see FIG. 2). The nesting surfaces 170, 172 help provide a snug fit of the syringe body 12 in the holder 14.

With reference to FIG. 5, another handle 200 is provided that may be used to connect the body 30 to a support structure. The handle 200 includes end portions 202, 204 and a loop portion 206 extending therebetween. The handle 200 also includes a hook 208 that may be looped over a structure to assist in hanging the handle 200 from a support structure. The handles 16, 200 may be releasably connected to the body 30 to permit a user to select the handle 16, 200 for a particular application. The body 30 and one or more of the handles 16, 200 may be provided in a kit with the syringe body 12 and tube 22.

In one embodiment, the holder 14 is made of one or more plastic materials, such as polypropylene or acrylonitrile butadiene styrene (ABS), and may be manufactured using an injection molding process. For example, the body 30 may be made using a one-shot injection molding process. The body 30 and the handles 16, 200 may be made of different materials. For example, the body 30 may be made of a first polypropylene having a first shore durometer hardness and the handles 16, 200 may be made of a second polypropylene having a different, second shore durometer hardness.

In one approach, the system 10 is used to administer a formulated food solution by first positioning the syringe body 12 in the body 30 of the holder 14. Next, the handle 200 (for example) is attached to the body 30 and the tube 22 is connected to the syringe body tip 26. The tube 22 is connected to the patient's feeding tube. The holder 14 and syringe body 12 therein are then hung on a structure such as the intravenous pole 18 or a door. The interior volume 140 of the syringe body 12 is filled with the desired volume of the formulated food solution, which the patient can visually confirm using the exposed calibrations 145. Gravity draws the formulated food solution into the tube 22, into the patient's feeding tube, and into the patient's stomach.

Figure 6:
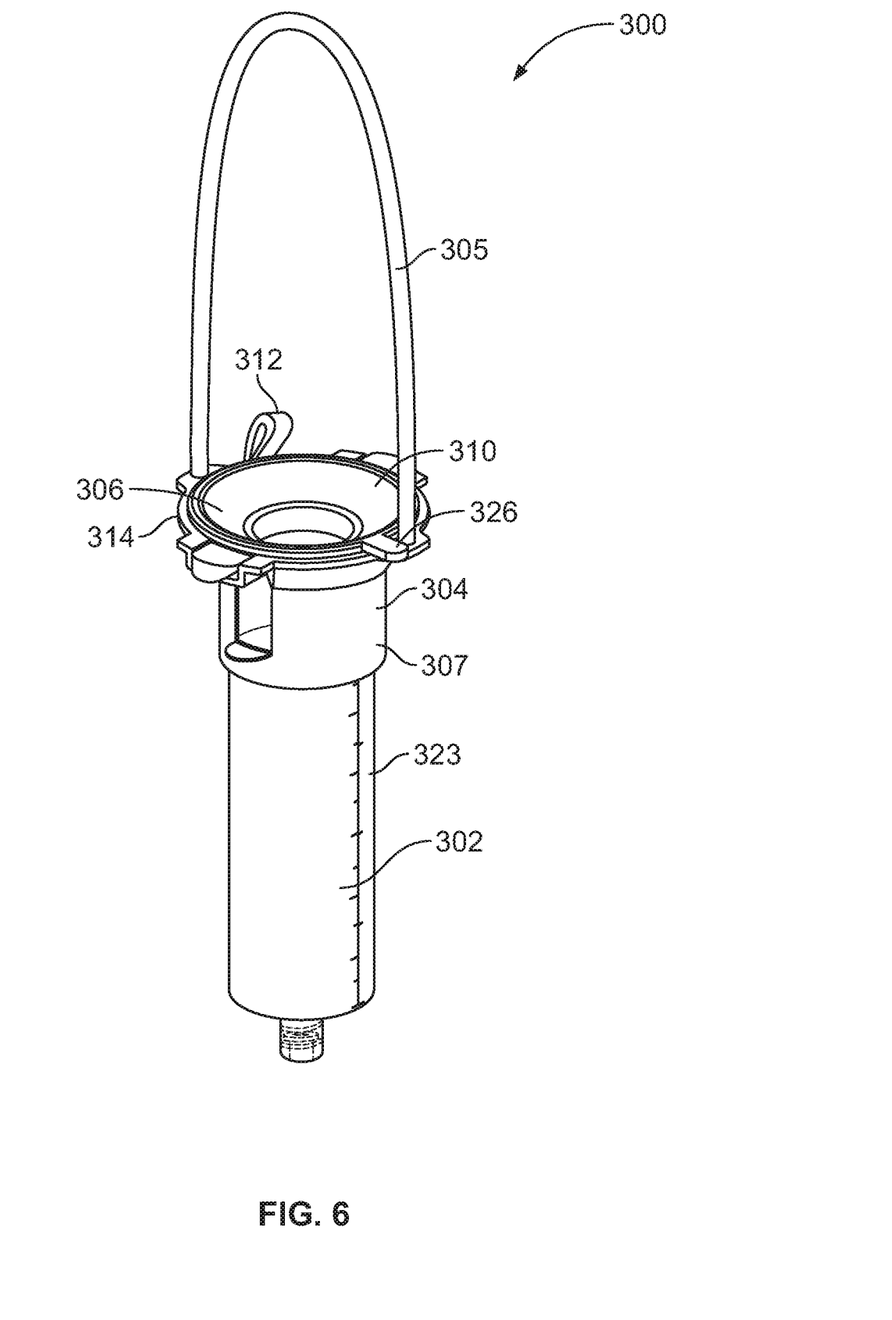
FIG. 6 is a perspective view of a formulated food solution delivery system including a holder, a syringe body received in the holder, and a cap of the holder in a closed position wherein the cap covers an opening of the syringe body.

With reference to FIG. 6, a formulated food solution delivery system 300 is provided that is similar in many respects to the system 10 discussed above such that differences between the systems 10, 300 will be highlighted. The formulated food solution delivery system 300 includes a syringe body 302 and a holder 304. The holder 304 includes a handle 305 and a lid 306. The syringe body 302 includes an opening 308 (see FIG. 7) for receiving formulated food solution and the lid 306 is movable between a closed position (see FIG. 6) wherein the lid 306 covers the opening 308 and an open position (see FIG. 7) wherein the opening 308 is uncovered. By covering the opening 308, the lid 306 resists egress of formulated food solution outward through the opening 308 from within the syringe body 302. This reduces the risk of a user spilling the formulated food solution such as if the user inadvertently bumps the formulated food solution delivery system 300 during a feeding.

The lid 306 may be made of a flexible material, such as a polypropylene, and may be made of the same material as the handle 305. The lid 306 includes a cover portion 310 connected to a flange 314 of the holder 304 by a connector such as a tether 312. In one embodiment, the lid 306 has a unitary, one-piece construction including the cover portion 310 and the tether 312. The tether 312 is elongate and includes a barb configured to fit in an opening of a flange 314 of a body 307 of the holder 304.

Figure 7:
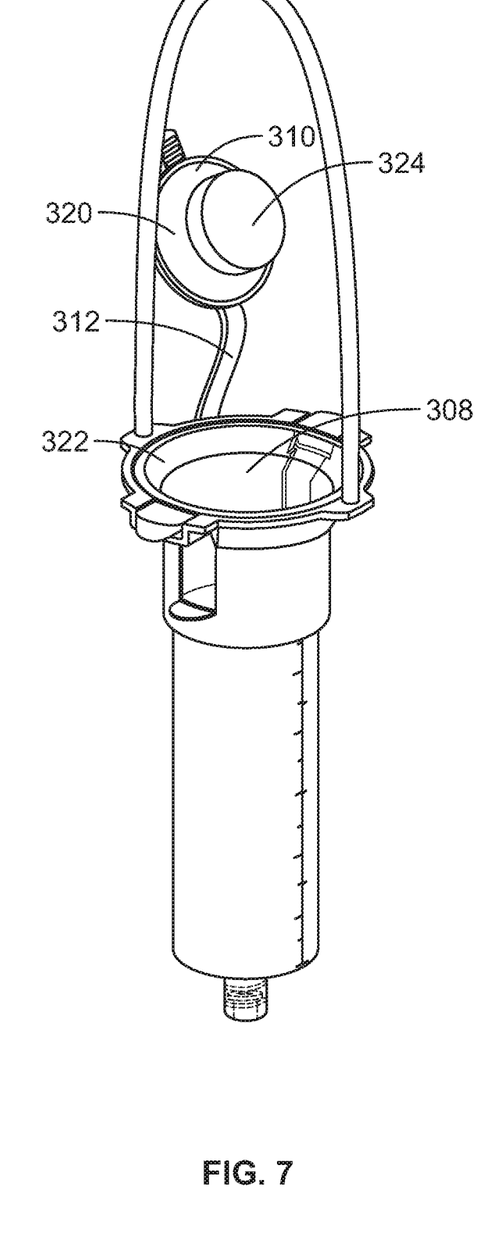
FIG. 7 is a perspective view similar to FIG. 6 showing the cap in an open position.

The cover portion 310 has a frustoconical portion 320 that seats against a frustoconical portion 322 of the syringe body 302. The cover portion 310 further includes a plug portion 324 configured to occlude the opening 308 of the syringe body 302. For example, the syringe body 302 may have a cylindrical wall 323 with an inner diameter and the plug portion 324 of the lid 306 has an outer diameter larger than the inner diameter. This causes the plug portion 324 to form a press fit with the cylindrical wall 323 when the lid 306 is in the closed position. The press fit between the lid 306 and the syringe body 302 provides a seal that resists egress of formulated food solution outward through the opening 308 of the syringe body 302. To open the lid 306, the user pulls upward on a tab 326 of the lid 306 to disengage the plug portion 324 of the lid 306 from within the opening 308 of the syringe body 302.

While there have been illustrated and described particular embodiments of the present invention, it will be appreciated that numerous changes and modifications will occur to those skilled in the art, and it is intended for the present invention to cover all those changes and modifications which fall within the scope of the appended claims.

What is claimed is:

1. A holder for a syringe body of a formulated food solution delivery system, the holder comprising:
a handle configured to be hung on a support;
a body connected to the handle and having a central opening for receiving a barrel of the syringe body, the body having an upper, collar-receiving region and a lower region each having a transverse cross-sectional area, the transverse cross-sectional area of the upper region having a frustoconical wall portion and being larger than the transverse cross-sectional area of the lower region, the lower region having an annular wall portion for extending around the syringe body barrel, the body configured to keep the syringe body upright with the handle hung on the support; and
at least one alignment portion of the body configured to engage at least one protrusion of the syringe body and resist turning of the syringe body in the central opening of the body, wherein the at least one alignment portion of the body includes at least one opening having a first portion in the frustoconical wall portion and a second portion in the annular wall portion.

2. The holder of claim 1 wherein the body is tubular and includes a wall portion extending completely around the central opening.

3. The holder of claim 1 wherein the at least one opening includes a pair of through openings on opposite sides of the body sized to receive protrusions of the syringe body.

4. The holder of claim 1 wherein the at least one opening includes a pair of pockets on opposite sides of the body configured to receive protrusions of the syringe body, each pocket having a floor arranged to extend below one of the protrusions and resist pull-through of the syringe body through the body.

5. The holder of claim 4 wherein each pocket includes a pair of side walls upstanding from the floor to inhibit rotary movement of the protrusion of the syringe body received in the pocket.

6. The holder of claim 1 wherein the upper collar-receiving portion includes at least one flat flange extending radially outward from the frustoconical wall portion and the handle includes an end portion connected to the at least one flat flange and extending away from the at least one flat flange generally normal to the at least one flat flange.

7. The holder of claim 1 wherein the central opening of body extends along a central, longitudinal axis and the at least one opening of the body includes a pair of laterally extending through openings of the body sized to receive a pair of protrusions of the syringe body.

8. The holder of claim 1 wherein the handle is elongated and includes a first end portion configured to be releasably connected to the body and an opposite, second end portion configured to be releasably connected to the body.

9. The holder of claim 1 wherein the handle includes a hook.

10. A system for administering a formulated food solution, the system comprising:
a syringe body including a collar and a barrel;
at least one protrusion of the syringe body;
a handle configured to be hung on a support;
a holder body connected to the handle and having a central opening sized to receive the syringe body, the holder body having an upper, collar-receiving region and a lower region each having a transverse cross-sectional area, the transverse cross-sectional area of the upper region having a frustoconical wall portion configured to nest with a frustoconical wall of the collar of the syringe body and being larger than the transverse cross-sectional area of the lower region, the lower region having an annular wall portion; and
at least one alignment portion of the holder body configured to engage at least one protrusion of the syringe body and resist turning of the syringe body in the central opening of the holder body, wherein the at least one alignment portion of the body includes at least one opening sized to receive the at least one protrusion of the syringe body, the at least one opening having a first portion in the frustoconical wall portion and a second portion in the annular wall portion.

11. The holder of claim 10 further comprising a lid movable between a closed position wherein the lid covers an opening of the syringe body and an open position wherein the lid is spaced from the opening of the syringe body.

12. The system of claim 10 wherein the at least one protrusion of the syringe body includes a first pair of protrusions of the barrel and the at least one opening includes a pair of openings on opposite sides of the holder body sized to receive the first pair of protrusions.

13. The system of claim 12 wherein the at least one protrusion of the syringe body includes a second pair of protrusions of the collar and the at least one opening of the holder body includes a pair of pockets on opposite sides of the holder body configured to receive the second pair of protrusions.

14. The system of claim 13 wherein each pocket includes a floor for extending below one of the second pair of protrusions and a pair of side walls upstanding from the floor to inhibit rotary movement of the one protrusion in the pocket.

15. The system of claim 10 wherein the barrel of the syringe body includes an annular side wall and the holder body includes an uninterrupted annular wall portion configured to extend completely around the annular side wall of the barrel of the syringe body.

16. The system of claim 10 wherein the upper collar-receiving portion of the holder body includes at least one flat flange extending radially outward from the frustoconical wall portion and the handle includes at least one end portion connected to the at least one flat flange and extending away from the at least one flat flange generally normal to the at least one flat flange.

17. The system of claim 10 wherein the handle is elongated and includes a first end portion connected to the holder body, a second end portion connected to the holder body on an opposite side of the holder body from the first end portion, and a loop portion connecting the first and second end portions.

18. A holder for a syringe body of a formulated food solution delivery system, the holder comprising:
a handle configured to be hung on a support;
a body connected to the handle and having a central opening for receiving a barrel of the syringe body, the body including an upper collar-receiving portion including a frustoconical wall portion and a lower barrel-receiving portion including an annular wall portion for extending around the syringe body barrel, the body configured to keep the syringe body upright with the handle hung on the support; and
at least one alignment portion of the body configured to engage at least one protrusion of the syringe body and resist turning of the syringe body in the central opening of the body, wherein the at least one alignment portion of the body includes at least one opening having a first portion in the frustoconical wall portion and a second portion in the annular wall portion.

19. The holder of claim 18 wherein the upper collar-receiving portion includes at least one flat flange extending radially outward from the frustoconical wall portion and the handle includes an end portion connected to the at least one flat flange and extending away from the at least one flat flange generally normal to the at least one flat flange.

* * * * *

UNITED STATES PATENT AND TRADEMARK OFFICE
CERTIFICATE OF CORRECTION

PATENT NO. : 10,765,798 B2
APPLICATION NO. : 16/256414
DATED : September 8, 2020
INVENTOR(S) : Timothy Mackelfresh et al.

Page 1 of 1

It is certified that error appears in the above-identified patent and that said Letters Patent is hereby corrected as shown below:

In the Claims

In Claim 11 (Column 6, Line 56), delete "holder" and insert -- system --, therefor.

Signed and Sealed this
Third Day of November, 2020

Andrei Iancu
*Director of the United States Patent and Trademark Office*